United States Patent
Kennedy et al.

(10) Patent No.: US 8,344,170 B2
(45) Date of Patent: Jan. 1, 2013

(54) POLY (CYCLOSILOXANE) COMPOSITION AND METHOD OF SYNTHESIS THEREOF

(75) Inventors: Joseph P. Kennedy, Akron, OH (US); Pious Kurian, Aurora, IL (US)

(73) Assignee: The University of Akron, Akron, OH (US)

( * ) Notice: Subject to any disclaimer, the term of this patent is extended or adjusted under 35 U.S.C. 154(b) by 669 days.

(21) Appl. No.: 10/525,284

(22) PCT Filed: Aug. 15, 2003

(86) PCT No.: PCT/US03/25661
§ 371 (c)(1), (2), (4) Date: Aug. 30, 2005

(87) PCT Pub. No.: WO2004/016670
PCT Pub. Date: Feb. 26, 2004

(65) Prior Publication Data
US 2006/0106187 A1    May 18, 2006

Related U.S. Application Data

(60) Provisional application No. 60/404,351, filed on Aug. 16, 2002.

(51) Int. Cl.
C07F 7/08 (2006.01)
C08G 77/08 (2006.01)

(52) U.S. Cl. .............. 556/451; 528/15; 528/21; 528/24; 528/32

(58) Field of Classification Search .............. 528/15, 528/21, 24, 32; 556/451
See application file for complete search history.

(56) References Cited

U.S. PATENT DOCUMENTS

| | | | |
|---|---|---|---|
| 5,017,671 A | 5/1991 | Bilgrien et al. | |
| 5,298,589 A | 3/1994 | Buese et al. | |
| 5,334,688 A | 8/1994 | Loo | |
| 5,347,028 A | 9/1994 | Buese et al. | |
| 5,373,077 A | 12/1994 | Loo | |
| 5,395,956 A | 3/1995 | Haines et al. | |
| 5,635,250 A | 6/1997 | Blum et al. | |
| 6,080,829 A | 6/2000 | Tapsak et al. | |
| 6,201,091 B1 | 3/2001 | Halloran et al. | |
| 6,207,781 B1 | 3/2001 | Halloran et al. | |
| 6,214,937 B1 | 4/2001 | Kennedy et al. | |
| 6,284,859 B1 | 9/2001 | Hupfield et al. | |
| 6,291,623 B1 | 9/2001 | Paulasaari et al. | |
| 6,353,075 B1 | 3/2002 | Hupfield et al. | |
| 6,365,698 B1 | 4/2002 | Goldslager et al. | |

*Primary Examiner* — Elvis O Price
(74) *Attorney, Agent, or Firm* — Renner Kenner Greive Bobak Taylor Weber

(57) ABSTRACT

A poly(cyclosiloxane) network comprises the hydrosilation reaction product of a cyclosiloxane of the formula (I) wherein R and $R^2$ are the same or different for each siloxane moiety of hydrogen, an alkyl group, an aryl group, and a cycloalkyl group, and wherein n is an integer from 3 to 8, wherein the cyclosiloxanes are joined by moieties selected from the group consisting of oxygen atoms, linear silanols, branched silanols, halosilanes, alkoxysilanes, vinyl silanes, allyl silanes, vinyl siloxanes, and allyl siloxanes, wherein the Si—O bonds of the cyclosiloxanes are substantially unrearranged compared to the cyclosiloxane precursors of the network. A process for the preparation of a poly(cyclosiloxane) network comprises providing a cyclosiloxane; providing a crosslinking group selected from the group consisting of linear silanols, branched silanols, halosilanes, alkoxysilanes, vinyl silanes, allyl silanes, vinyl siloxanes, and allyl siloxanes; contacting the cyclosiloxane and crosslinking group under condensation reaction conditions such that the crosslinking groups provide Si—O—Si linkages between the cyclosiloxane moieties to form a poly(cyclosiloxane) network composition.

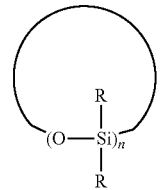

5 Claims, 5 Drawing Sheets

POLY (CYCLOSILOXANE) COMPOSITION AND METHOD OF SYNTHESIS THEREOF

This application gains priority from U.S. Provisional Application No. 60/404,351, filed on Aug. 16, 2002.

STATEMENT REGARDING FEDERALLY SPONSORED RESEARCH OR DEVELOPMENT

This invention was made with government support under cooperative agreements awarded by the National Science Foundation under Grant No. 99-88808. The government may have certain rights to the invention.

TECHNICAL FIELD

This invention relates generally to the synthesis of new poly(cyclosiloxane) compositions and networks. More particularly, the present invention relates to the co-polymerization of polycyclosiloxanes and specific linking groups to provide strong, elastic, thermally stable polymer networks.

BACKGROUND OF THE INVENTION

Many cyclic polysiloxanes, including pentamethylcyclopentasiloxane (sometimes referred to hereinafter as $D_5H$) have been commercially available for a number of years. At one time, these materials seemed promising for use in medical applications. They are known to be useful as crosslinkers in silicone coatings and encapsulating materials used in the electronic industry, as well as for other electronic applications, such as composites and adhesives. Hence, synthetic methods therefor are known in the art.

For example, Haines et al U.S. Pat. No. 5,395,956, discloses a process for the synthesis of organohydrogensiloxanes, namely cyclic organohydrogensiloxanes. A hydrolyzate intermediate is rearranged via an acidic rearrangement catalyst, such as a sulfonated divinylbenzenestyrene copolymer resin, to form a cyclic organohydrogen-siloxane having the formula of formula I.

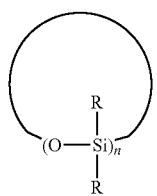

(I)

where n=3 to 12. As noted in the patent, such polysiloxanes are known in the art, but this process for its production provides minimal loss of siloxanes due to crosslinking of the siloxanes to high molecular weight byproducts. Accordingly, cyclic polysiloxanes such as pentamethylcyclopentasiloxane are known.

It is also known to create homopolymers of cyclic polysiloxanes such as pentamethylcyclopentasiloxane. For example, commonly owned U.S. Application No. 60/329,678 discloses the polymerization of cyclosiloxane molecules having the formula shown in formula I above, where R is the same or different for each cyclosiloxane moiety and is selected from the group consisting of a hydrogen, an alkyl group, an aryl group, and a cycloalkyl group, and wherein n is an integer from 3 to 8, and wherein each cyclosiloxane moiety is bound to at least two other cyclosiloxane moieties via each of at least two Si—O—Si functionalities. Polymerization is accomplished by oxidizing each cyclosiloxane moiety with water in the presence of a catalyst to form at least two Si—OH groups from the Si—H groups present on each ring and immediately thereafter condensing the cyclic rings such that the SiOH groups on each ring react to provide Si—O—Si linkages between the cyclosiloxane moieties to form a poly(cyclosiloxane) network composition. When pentamethylcyclopentasiloxane is polymerized, the product is poly(pentamethylcyclopentasiloxane), which is also referred to as $PD_5$.

Crosslinking different derivatives of cyclic polysiloxanes is also known in the art. In particular, Loo, U.S. Pat. No. 5,334,688, discloses a crosslinked polymer or crosslinkable prepolymer, which is the hydrosilation reaction product of a cyclic polysiloxane, an organosilicon compound having at least two ≡Si—H groups, and an optional third ingredient, an aromatic polyene having at least one carbon-carbon double bond. In Loo, U.S. Pat. No. 5,373,077, a divisional of the '688 patent, the aromatic polyene is a required ingredient. These crosslinked polymers, while technically polycyclosiloxanes, are limited to hydrosilation reactions between cyclic polysiloxanes having the formula

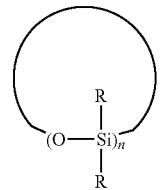

wherein R is a saturated, substituted or unsubstituted alkyl or alkoxy group or a substituted or unsubstituted aryl or aryloxy group, $R^1$ is a substituted or unsubstituted hydrocarbon group having at least one nonaromatic carbon-carbon double bond reactive via hydrosilation, and n is 3 or 4; and cyclic polysiloxanes having at least two Si—H groups. However, these compositions are prepared only by way of a hydrosilation reaction wherein a Si—H group reacts with a vinyl or allyl group to provide the Si—O—Si linkages.

Similarly, other multiple component networks have also been prepared. For example, U.S. Pat. Nos. 5,298,589 and 5,347,028 disclose "living rubbers" made from a cyclosiloxane and a polysiloxane. The polysiloxane is selected from the group consisting of a linear polydimethylsiloxane, a polydimethylcyclosiloxane containing between about 6 and about 50 silicon-oxygen bonds, a linear or cyclic block copolymer of polydimethylsiloxane and a non-siloxane organic polymer, and a linear or cyclic random copolymer of a siloxane of the formula $Si(R)(R^1)O$ where R and $R^1$ are different and are selected from the group consisting of hydrogen, $C_1$-$C_{18}$ hydrocarbon and $C_2$-$C_{18}$ hydroxyalkyl. The cyclosiloxane and polysiloxane are polymerized by hydrosilation reactions to form polycyclosiloxanes. The resulting polycyclosiloxanes are chains of cyclosiloxanes that are linked via crosslinking moieties that contain alkyl groups. That is, the siloxane moieties of the cyclosiloxanes are linked via —R—Si—R— or —R—Si—O—Si—R— linking groups, where R is a hydrocarbon. Alternatively, a cyclosiloxane may be contacted with chlorine gas to form a chlorosilane. The chlorosilane is then contacted with water to hydrolyze it and form a silanol or a siloxane, which is then heated to form a liquid polycyclosiloxane. The polycyclosiloxanes disclosed in these patents are essentially linear chains of cyclosiloxanes with minimal branching. This structure dictates their liquid state. These polycyclosiloxanes are then treated with a strong acid, which reportedly rearranges the Si—O bonds, to cure the composition and form thermally reversible rubbers.

Another example of multicomponent networks is provided by commonly owned U.S. application Ser. No. 09/833,774, the disclosure of which is hereby incorporated by reference herein, which discloses multicomponent networks comprising the reaction product of a plurality of multifunctional, allyl-terminated polyethylene glycols linked to a plurality of multifunctional siloxanes having at least two SiH moieties for each siloxane.

However, the need continues to exist for additional silicon-based compositions that exhibit thermal and oxidative resistance and flexibility. A need also exists for a method of making a polycyclosiloxane network that does not depend on treatment of a polycyclosiloxane with a strong acid to form the network.

BRIEF SUMMARY OF THE INVENTION

It is, therefore, an aspect of the present invention to provide a silicon-based composition that exhibits thermal and oxidative resistance.

It is also an aspect of the present invention to provide a silicon-based composition that is flexible.

It is another aspect of the present invention to provide a method of synthesizing a silicon-based composition that does not require treatment with a strong acid.

It is another aspect of the present invention to provide a silicon-based composition that has a $T_g$ below $-140°$ C.

At least one or more of the foregoing aspects, together with the advantages thereof over the known art relating to polysiloxanes, which shall become apparent from the specification which follows, are accomplished by the invention as herein after described and claimed.

In general, the present invention provides a poly(cyclosiloxane) network comprising the hydrosilation reaction product of a cyclosiloxane of the formula

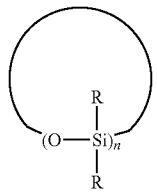

wherein R and $R^2$ are the same or different and are selected from the group consisting of hydrogen, an alkyl group, an aryl group, and a cycloalkyl group, and wherein n is an integer from 3 to 8; and moieties selected from the group consisting of linear silanols, branched silanols, halosilanes, alkoxysilanes, vinyl silanes, allyl silanes, vinyl siloxanes, and allyl siloxanes, wherein the network comprises Si—O bonds that are substantially unrearranged compared to the cyclosiloxane precursors of the network.

The present invention also provides a process for the preparation of a poly(cyclosiloxane) network. The process comprises providing a cyclosiloxane, providing a crosslinking group selected from the group consisting of linear silanols, branched silanols, halosilanes, alkoxysilanes, vinyl silanes, allyl silanes, vinyl siloxanes, and allyl siloxanes, contacting the cyclosiloxane and crosslinking group under condensation reaction conditions such that the crosslinking groups provide Si—O—Si linkages between the cyclosiloxane moieties to form a poly(cyclosiloxane) network composition.

DETAILED DESCRIPTION OF THE INVENTION

Figure 1:
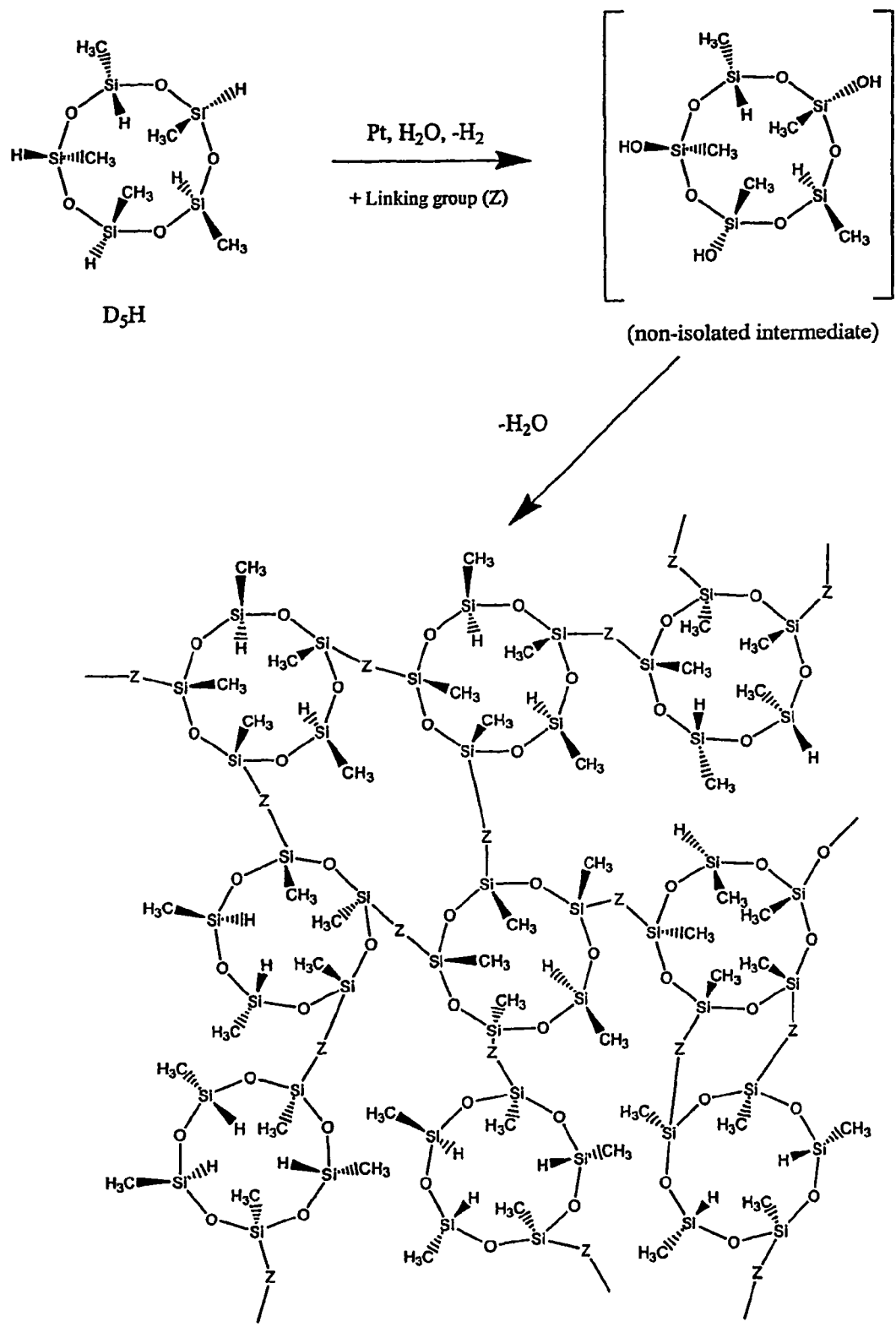
FIG. 1 is an example of an idealized structure of a network according to the present invention.

As disclosed hereinabove, the present invention is directed toward the synthesis of a network comprising a reaction product of a polycyclosiloxane and a linking group selected from the group consisting of linear silanols, branched silanols, halosilanes, alkoxysilanes, and vinyl or allyl silanes or siloxanes. The polycyclosiloxanes may be represented by the formula

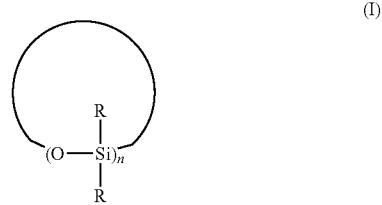

wherein each R is the same or different for each siloxane moiety and is selected from the group consisting of a hydrogen, a substituted or unsubstituted alkyl group, a substituted or unsubstituted aryl group, and a substituted or substituted cycloalkyl group, and wherein n is an integer from 3 to 8. The polycyclosiloxane network may be represented by formula II.

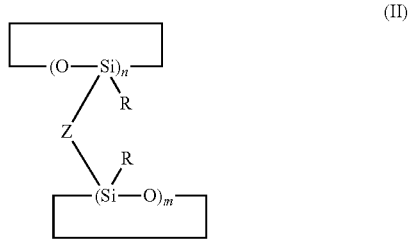

In formula II, n and m can be the same or different, Z is a linking group, and a majority of the siloxane moieties (—HSiR—O—) are crosslinked to siloxane moieties of adjacent cyclosiloxanes such that each cyclosiloxane is linked to multiple adjacent cyclosiloxanes to form the polycyclosiloxane network. In one particular embodiment, at least 60 percent of the siloxane moieties are crosslinked to siloxane moieties of adjacent cyclosiloxanes.

The present invention provides a network having extremely good thermal stability, resistance to harsh chemical environments and a low glass transition temperature. This contrasts with polycyclosiloxane living rubbers which contain an essentially linear chain of cyclosiloxanes that are then cross linked by rearranging the Si—O bonds by curing with a strong acid. The present composition forms a network while leaving the existing Si—O bonds of the polycyclosiloxane component intact.

Preferably, the compositions formed are methylcyclohydrosiloxane-containing networks. Thus the R in the formula I above is a methyl group. A preferred cyclic polysiloxane is pentamethylcydopentasiloxane. Other examples of preferred cyclic polysiloxanes include, for example, trimethylcydotrisiloxane, tetramethycyclotetrasiloxane (sometimes referred to hereinafter as D$_4$H), hexamethylcyclohexasiloxane (sometimes referred to hereinafter as D$_6$H), heptamethylcycloheptasiloxane, and octakis(ditnethylsiloxy)T8-silsesquioxane (sometimes referred to hereinafter as T$_8$H).

It will be appreciated, however, that the cyclic polysiloxanes of the present invention can be substituted or unsubstituted, provided that the cyclic polysiloxane contains at least two Si—H bonds. Thus, alkylcyclohydrosiloxanes can be employed, including hydrocarbon substituted cyclopentasiloxanes. It is believed and anticipated that any cyclic or aryl hydrocarbon substituted or unsubstituted cydopolysiloxane can be polymerized as well by the synthesis method provided herein. Examples of aryl cyclosiloxanes include, for example, pentaphenylcyclopentasiloxane, or hydrocarbon substituted aryl cyclopentasiloxane. Cyclic derivatives of cyclosiloxanes may also be used including, for example, tritolylcyclotrisiloxane, and pentatolylcyclopentasiloxanes. Cyclic alkyl substituted cyclosiloxane derivatives including, for example, tri(cyclohexyl)cyclotrisiloxane, or penta(cyclohexyl)cyclopentasiloxanes may also be used.

As mentioned above, the method of the present invention includes the use of linking groups selected from the group consisting of linear silanols, branched silanols, halosilanes, alkoxysilanes, and vinyl or allyl silanes or siloxanes. Included in these categories are linear ditelechelics of formula III including linear ditelechelic vinyl or allyl silanes and polysiloxanes, linear polysiloxanes with pendent vinyl or allyl groups of formula IV, branched silanes and polysiloxanes of formulae V-V-III, linear polysilanols, polyalkoxysiloxanes and polyhalosiloxanes having non-terminal functionalities according to formula IX, and branched polysilanols, polyalkoxysilanes and polyhalosiloxanes of formulae VI and X-XII.

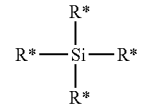

(III)

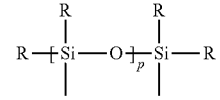

(IV)

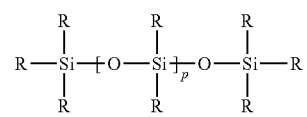

(V)

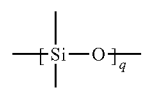

(VI)

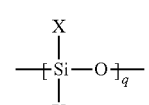

(VII)

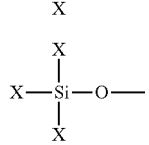

(VIII)

$$\begin{array}{c} | \\ -\!\!\!+\!\!Si-O\!\!+\!\!\!- \\ | \\ X \end{array}_q$$

(IX)

$$\begin{array}{c} X \\ | \\ -\!\!\!+\!\!Si-O\!\!+\!\!\!- \\ | \\ X \end{array}_q$$

(X)

$$\begin{array}{c} X \\ | \\ X-\!\!Si-O-\!\!\!- \\ | \\ X \end{array}$$

(XI)

In formulae III-XI, p is 0-200, q is 1-100, R is a $C_1$-$C_4$ alkyl, R* is a vinyl, an allyl, a hydride, a hydroxyl, a halogen or a $C_1$-$C_4$ alkoxy and X is a hydroxyl, a halogen or a $C_1$-$C_4$ alkoxy.

The polymerization of these networks is conducted by oxidation of the SiH group on the cyclosiloxane moiety to form SiOH groups, followed immediately by condensation of the cyclic ring to form complex aggregates of cyclosiloxane moieties. More particularly, it is believed that the Si—OH groups are condensed to Si—O—Si to form Si—O—Si linkages between the cyclosiloxane rings. Alternatively, the SiH groups may react with a vinyl or allyl group when these groups are present in a crosslinking species to form Si—R—Si—R—Si linkages where R is $CH_2CH_2$ or $CH_2CH_2CH_2$.

Polymerization of these cyclosiloxanes by oxidation and polycondensation is conducted with water in the presence of a catalyst. Only an amount of water, whose molar concentration is equal to or less than the molar concentration of the Si—H groups in the system, is necessary for the reaction to occur.

The reaction may be conducted with or without solvents. When solvents are employed, it may be any typical aromatic, solvent including, by way of example, benzene, xylene, toluene, hexane, cyclohexane, heptane, cycloheptane, and the like. The most preferred solvent is toluene.

The catalyst may be a platinum-based catalyst system, including a Karstedt's system (a platinum divinyl complex in toluene or xylene, such as is available from United Chemical Technologies), chloroplatinic acid in isopropanol bis(acetonitrile)platinum dichloride, bis(benzonitrile)platinum dichloride, platinum on carbon, platinum dichloride, cyclooctadieneplatinum dichloride, dicyclopentadieneplatinum dichloride and metallocene platinum systems. The platinum catalyst is present in an amount of 0.0005% to 0.10% by weight of platinum, based on the weight of the monomers, preferably 0.001% to 0.05%, and most preferably 0.005% to 0.01%. Most preferred is the Karstedt catalyst, $Pt_2\{[(CH_2=CH)Me_2Si]_2O\}_3$. A tin-containing catalyst such as tin octanoate may also be used as a catalyst. Likewise, other metal-containing complexes, for example, titanium complexes, zirconium complexes and rhodium complexes, are also suitable catalysts.

The reaction of cyclosiloxanes in the polymerization reaction may be illustrated with reference to the formation of a network of cyclosiloxane moieties at least partially utilizing a crosslinking group (Z). The resulting poly(pentamethyl-cyclopentasiloxane) is shown in FIG. 1. It will be appreciated that the polycyclosiloxane shows only a representative microarchitecture of the polymer, and that the present invention should not be limited to this one polymer, it being understood that the present invention, as envisioned, includes other cyclic polysiloxanes of the same or similar microstructure as $D_5H$ and various linking groups as described above. It should also be understood that the cyclosiloxane may partially condense with other cyclosiloxanes within the polycyclosiloxane network, depending on the concentration of the crosslinker (Z). In such cases, oxygen present in the Si—OH group described above may act as the linking group in place of linking group Z, enabling direct linkage of cyclosiloxane moieties without a linking group.

As shown in FIG. 1, the polymerization starts by the interaction between $D_5H$ and $Pt/H_2O$, a reaction in which the monomer is converted to an intermediate of cyclopentanesiloxane rings in which at least some of the SiH groups have been converted to SiOH groups. Gaseous hydrogen is evolved during the production of this intermediate, which has not been isolated. This Pt catalyzed oxidation in the presence of water ($SiH+H_2O\rightarrow SiOH+H_2$) is believed to produce gaseous $H_2$ that leads to an intense bubbling observed during the initial phases of the synthesis. This energetically strongly favored conversion is driven by the formation of strong Si—O bonds from relatively weaker Si—H linkages and by the entropy gain of gaseous $H_2$ evolution. The cyclosiloxane intermediate carrying multiple Si—OH groups immediately starts to undergo polycondensations. Obviously, oxidation of Si—H and polycondensation of SiOH with or without a crosslinking group proceed simultaneously. The water used for the oxidation is recovered by condensation (2 Si—OH→Si—O—Si+$H_2O$, or 2 Si—OH+Z→Si—Z—Si+$H_2O$). The final product is a random aggregate of condensed cyclosiloxanes comprising a great variety of linearly connected and crosslinked rings.

The resulting polycyclosiloxane network displays a number of desirable properties. These include thermal and oxidative resistance and flexibility. Therefore, the compositions made according to this invention may be characterized as flexible ceramics. This contrasts with previous polycyclosiloxanes and polycyclosiloxane networks such as Buese's "living rubbers" mentioned above. Those rubbers were thermoplastic, that is, they can be heated and melted, returning to a rubbery state upon cooling. The polycyclosiloxane networks of the present invention are thermoset. They display a high degree of thermal stability, remaining solid at temperatures well above 200° C., with very little weight loss.

In order to demonstrate practice of the present invention, the following examples are provided. The following are illustrative of the nature of the present invention and should not necessarily be construed as limiting the scope of the invention. Other materials and processing steps or conditions may be substituted as is known in the art for those materials, steps or conditions described herein, it being understood that the scope of the invention continues to reside in the invention as hereinafter claimed.

Appropriate amounts of $D_5H$ and a crosslinker ($CH_2=CH$—Si—O—Si—$CH=CH_2$, (divinyldisiloxane), $CH_2=CH(SiO)_5SiCH=CH_2$ (divinylhexasiloxane), or $HO(SiO)_5SiOH$ (dihydroxyhexasiloxane)) (1 gram (g)/50 milliliters (ml) solvent) were dissolved in toluene and placed in a 100 or 300 ml round bottom flask containing a magnetic stir bar. Under constant stirring, approximately 10 microliters (µl) of Karstedt's catalyst was added and the charge was stirred at about 80° C. for approximately 36 hours. A drop of water (about 0.3 ml) was added to the stirred solution and the charge was stirred for another 12 hours. A transparent, highly viscous fluid resulted, which was poured into Teflon or aluminum molds. Most of the toluene was evaporated overnight at room temperature. Crosslinking completed under the influence of ambient humidity at room temperature. The resulting films were dried under reduced pressure for about 2 days. The physical properties and certain visual observations regarding the resulting networks are listed in Tables 1-3.

TABLE 1

Networks from $D_5H$ and $CH_2CHSiOSiCHCH_2$

| | $D_5H:CH_2CHSiOSiCHCH_2$ | | | Weight Loss |
|---|---|---|---|---|
| Sample | Mole ratio | Weight ratio | $T_g$ (° C.) | (at 800° C.) |
| 1 | 4:1 | 87:13 | −161 | ~5% |
| 2 | 2:1 | 76:24 | −158 | ~5% |
| 3 | 1:1 | 61:38 | −162 | ~10% |
| 4 | 1:2 | 45:55 | −159 | ~15% |
| 5 | 1:2.5 | 39:61 | −155 | ~20% |

TABLE 2

Networks from $D_5H$ and $CH_2CH(SiO)_5SiCHCH_2$

| | $D_5H:CH_2CH(SiO)_5SiCHCH_2$ | | | Weight Loss |
|---|---|---|---|---|
| Sample | Mole ratio | Weight ratio | $T_g$ (° C.) | (at 1000° C.) |
| 6 | 4:1 | 71:29 | −159 | ~5% |
| 7 | 2:1 | 55:45 | −161 | ~5% |
| 8 | 1:1 | 38:62 | −160, −93 | ~5% |
| 9 | 1:2 | 23:77 | −160, −94 | ~7% |
| 10 | 1:2.5 | 19:81 | −161, −94 | ~13% |

TABLE 3

Networks from $D_5H$ and $HO(SiO)_5SiOH$

| | $D_5H:HO(SiO)_5SiOH$ | | | Weight Loss |
|---|---|---|---|---|
| Sample | Mole ratio | Weight ratio | $T_g$ (° C.) | (at 1000° C.) |
| 11 | 5:1 | 73:27 | — | ~1% |
| 12 | 4:1 | 68:31 | −156, −80 | ~1% |
| 13 | 3:1 | 62:38 | — | ~2% |
| 14 | 2:1 | 52:48 | −160, −95 | ~4% |
| 15 | 1:1 | 35:65 | −160, −97 | ~4% |
| 16 | 1:2 | 21:79 | −161, −97 | ~6% |
| 17 | 1:2.5 | 18:82 | −163, −110 | ~6% |

The overall composition and therefore, the properties of the network may be controlled by varying the relative amounts of cyclosiloxane and crosslinker. The percentage weight loss listed in Tables 1-3 determined by thermogravimetric analysis using a SDTA851e instrument from Mettler Toledo. The samples were heated in nitrogen at a rate of 10° C. per minute. The samples showed varying degrees of thermal stability, with the siloxane networks from $D_5H$ and HO(SiO)₅SiOH exhibiting a particularly high degree of thermal stability. While not wishing to condition patentability on any particular theory, it is believed that thermal stability is due to the fact that the crosslinking groups consist exclusively of polysiloxane moieties. It is further believed that the flexibility of the composition is inversely proportional to the $CH_2$ groups in the network.

It should be noted that some of the samples exhibit two glass transition temperatures (g). Again, while not wishing to condition patentability on any particular theory, it is believed that the second $T_g$ is provided when longer linear molecular chains are present in the cross-linking component of the network. The presence of the second $T_g$ indicates that phase separation occurs in the system and that long molecular chains such as polydimethylsiloxane (PDMS) exhibit their own $T_g$. The presence of two $T_g$s is not a requirement of the composition of the present invention.

Figure 2:
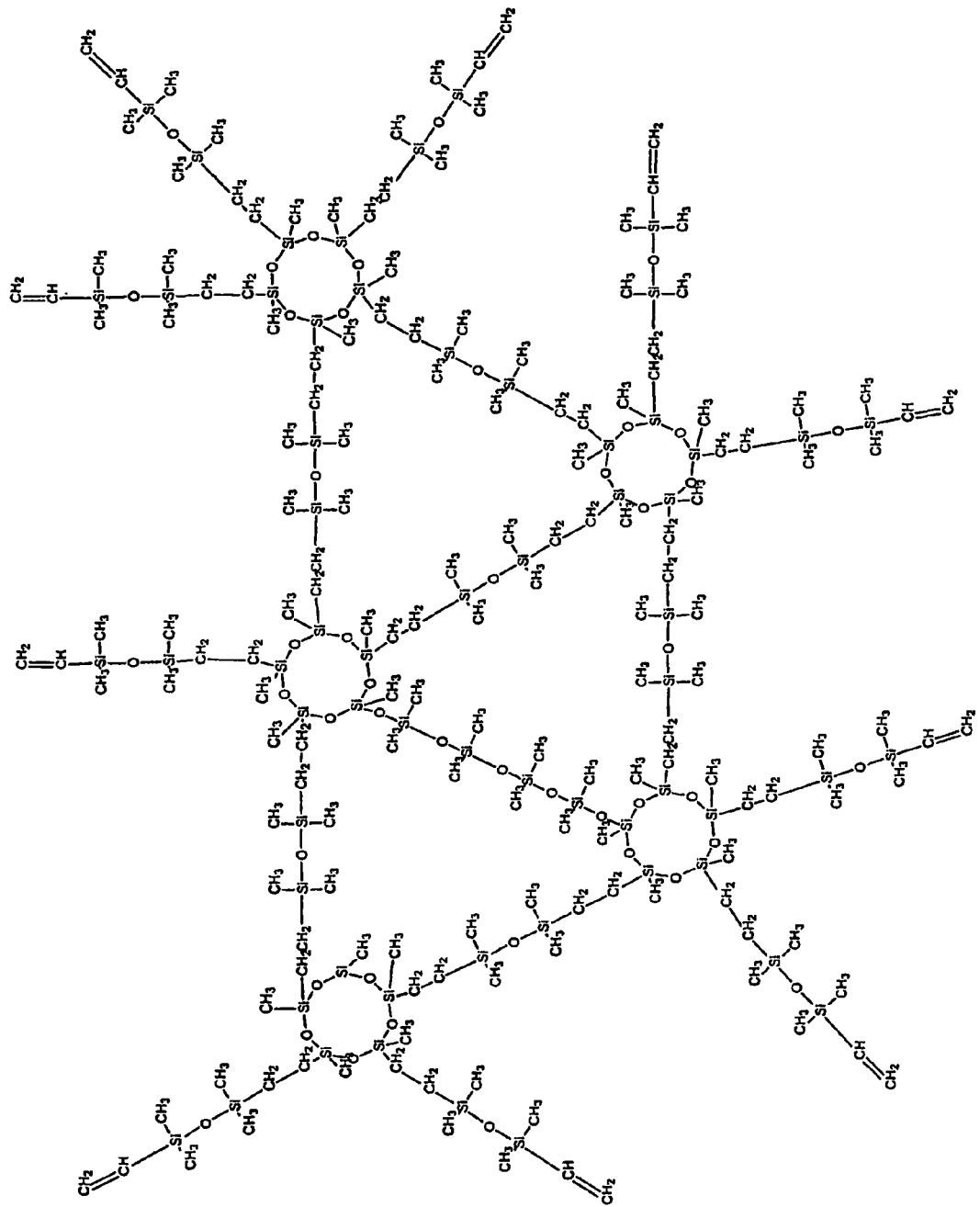
FIG. 2 is an idealized structure of a network obtained with $D_5H$ and a divinyldisiloxane at a molar ratio of less than approximately 1:2.5.
Figure 3:
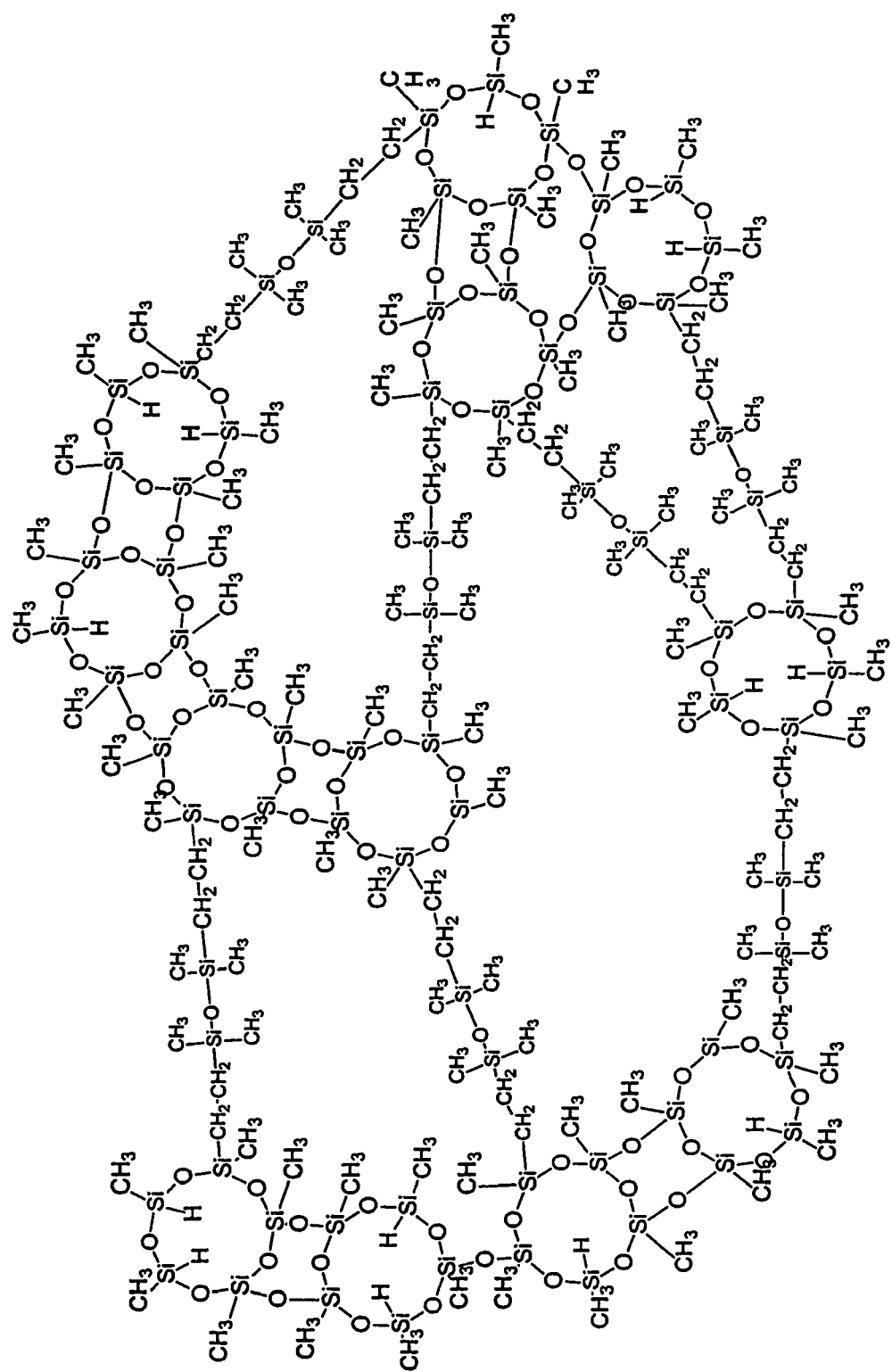
FIG. 3 is an idealized structure of a network obtained with $D_5H$ and a divinyldisiloxane at a molar ratio of approximately 2:1.
Figure 4:
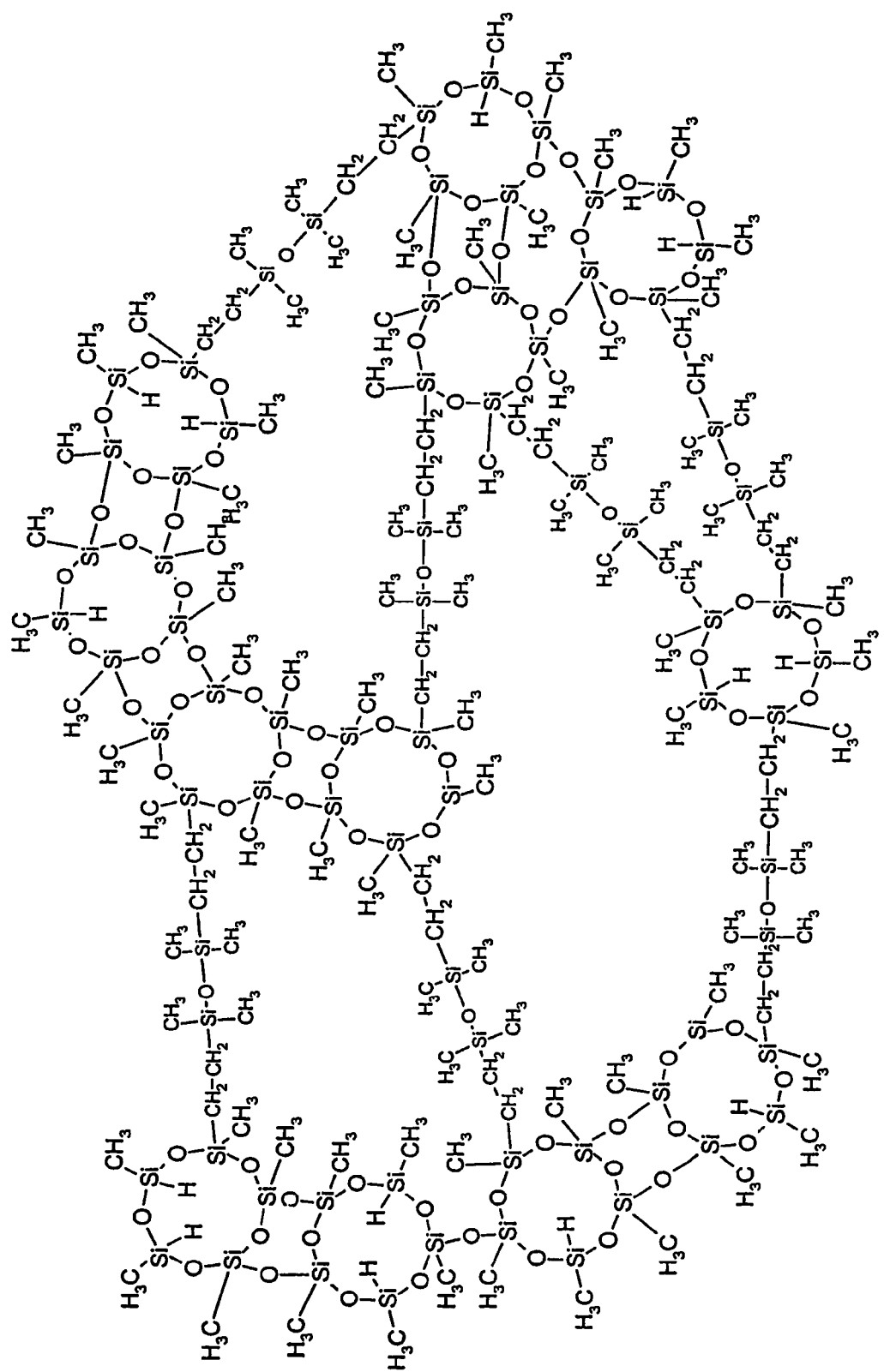
FIG. 4 is an idealized structure of a network obtained with $D_5H$ and a dihydroxypolysiloxane at a molar ratio of approximately 2:1.

Idealized structures of networks obtained according to the method of the present invention are shown in FIGS. 2-4. FIG. 2 is an idealized structure of a network obtained with $D_5H$ and a divinyldisiloxane at a $D_5H$:$CH_2CHSi(CH_3)_2OSi(CH_3)_2CHCH_2$ molar ratio of 1:greater than 2.5. It is believed that at such a ratio, unreacted pendent vinyl groups are present in the network. Such a network may therefore provide a useful intermediate for additional compounds due to the presence of the reactive vinyl groups. This provides an advantage over prior siloxane networks because prior networks only contained pendent methyl groups which could not be functionalized without destroying the network. The pendent vinyl groups of the networks of the present invention, however, can be easily functionalized, as will be apparent to one of skill in the art.

FIG. 3 is an idealized structure of a network obtained with $D_5H$ and a divinyldisiloxane at a molar ratio of $D_5H$:$CH_2CHSi(CH_3)_2OSi(CH_3)_2CHCH_2$ of approximately 2:1. Because of the relatively high concentration of $D_5H$ in the network, siloxane moieties within the cyclosiloxanes are believed to be linked both to the divinyldisiloxane lining groups, and directly to other siloxane moieties in other cyclosiloxanes to form a linking group consisting of an oxygen atom.

Another idealized structure of a network according to the present invention is shown in FIG. 4. FIG. 4 shows a network obtained with $D_5H$ and a dihydroxypolysiloxane at a molar ratio of $D_5H$:$HO[(CH_3)_2SiO]_nSiOH$ of approximately 2:1. As with the structure shown in FIG. 3, the relatively high concentration of $D_5H$ in the network allows siloxane moieties within the cyclosiloxanes to be linked to other siloxane moieties. The structure shown in FIG. 4 can be considered an idealized structure for sample 14 when n=5.

Figure 5:
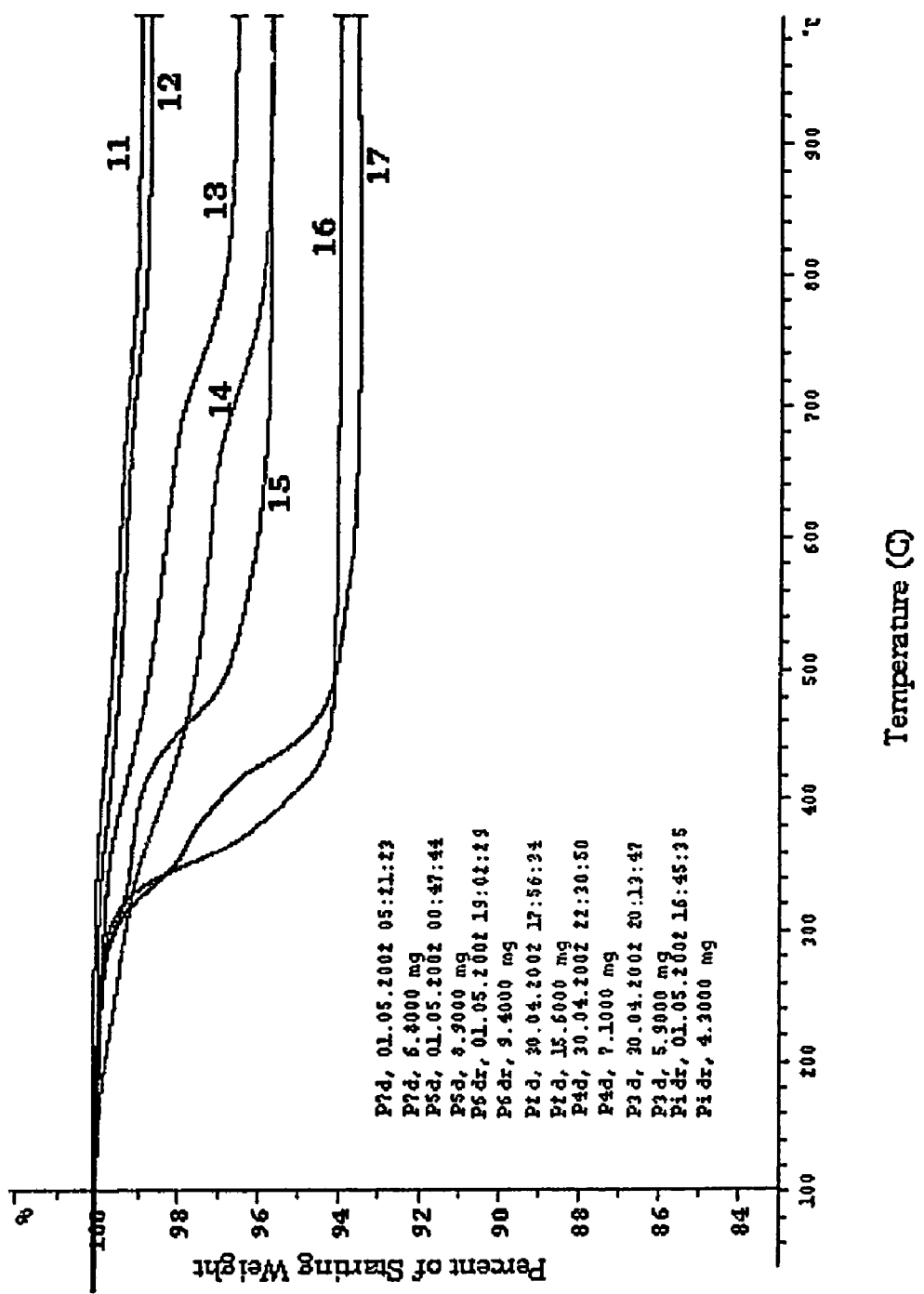
FIG. 5 is a graph showing the results of thermogravimetric analysis of several networks according to the present invention.

As mentioned above, the samples listed in Table 3 were analyzed by the thermogravimetric analysis. FIG. 5 is a graph showing the percentage weight loss for given temperatures for Samples 11-17. As shown in Table 3 and FIG. 5, the networks of the present invention can provide compositions that display about 6 percent weight loss or less when heated under nitrogen to 1000° C.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention pertains.

As used in this specification and the appended claims, unless a contrary meaning is clearly indicated:

"siloxane" shall be deemed to mean any group containing a —(Si—O)$_n$— moiety wherein n is a positive integer, and includes cyclosiloxanes;

"cyclosiloxanes" shall be deemed to include all those chemical species encompassed by the structure of formula I above;

"polycyclosiloxanes" are two or more cyclosiloxanes joined in any arrangement;

and a "polycyclosiloxane network" shall be deemed to include polycyclosiloxanes wherein at least a portion of the cyclosiloxane components are joined to each other in a substantially branched arrangement. By substantially branched is meant that at least about half of the cyclosiloxanes are joined to more than two other cyclosiloxanes.

Based upon the foregoing disclosure, it should now be apparent that the present invention is highly effective in providing a silicon-based composition that is both flexible and highly resistant to thermal and oxidative degradation. It is, therefore, to be understood that any variations evident fall within the scope of the claimed invention and thus, the selection of specific component elements can be determined without departing from the spirit of the invention herein disclosed and described.

We claim:

1. A poly(cyclosiloxane) network comprising the hydrosilation reaction product of:

a cyclosiloxane of the formula:

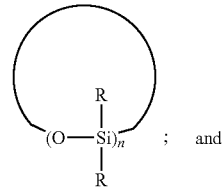

; and at least one crosslinking group selected from one or more of the following formulas:

(V)

(VI)

wherein R* is a hydride, wherein each R is the same or different for each siloxane moiety and is selected from the group consisting of hydrogen, an alkyl group, an aryl group, and a cycloalkyl group, and wherein n is an integer from 3 to 8, and wherein the silane compound contains three or more Si—H bonds and at least two of the three or more Si—H bonds on each molecule of the silane compound act as crosslinking sites.

2. The poly(cyclosiloxane) network of claim 1, wherein n is equal to 5.

3. The poly(cyclosiloxane) network of claim 1, wherein the molar ratio of cyclosiloxanes to reacted moieties is greater than 1:1.

4. The poly(cyclosiloxane) composition of claim 1, wherein the cyclosiloxane is selected trimethylcyclotrisiloxane, tetramethycyclotetrasiloxane, hexamethylcyclohexasiloxane, heptamethylcycloheptasiloxane, and octakis(dimethylsiloxy)T8-silsesquioxane.

5. The polycyclosiloxane network of claim 1, wherein the network is a thermoset composition.

* * * * *